US00PP18921P2

(12) United States Plant Patent
Zaiger et al.

(10) Patent No.: US PP18,921 P2
(45) Date of Patent: Jun. 10, 2008

(54) INTERSPECIFIC TREE 'LATE BRITTNEY'

(50) Latin Name: *Interspecific Prunus*
Varietal Denomination: Late Brittney

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 25 days.

(21) Appl. No.: 11/699,592

(22) Filed: Jan. 30, 2007

(51) Int. Cl.
*A01H 5/00* (2006.01)

(52) U.S. Cl. ..... Plt./180
(58) Field of Classification Search ..... Plt./180
See application file for complete search history.

*Primary Examiner*—Annette H Para

(57) ABSTRACT

A new and distinct variety of interspecific tree. The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, semi-spreading tree growth.
2. Heavy and regular production of large fruit maturing in the late season.
3. Fruit having firm flesh, holding firm on the tree 7 to 10 days after maturity (shipping ripe).
4. Fruit with very good flavor and shipping quality.
5. Fruit with an average Brix of 15.5° and a good balance between acid and sugar.
6. Fruit with an attractive yellow-orange skin color.

1 Drawing Sheet

Botanical classification: *Interspecific Prunus* species.

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our varieties that the present variety of interspecific tree was originated and asexually reproduced by us in our experimental orchard located near Modesto, Stanislaus County, Calif.

PRIOR VARIETIES

Among the existing varieties of interspecific, plum and apricot trees, which are known to us, and mentioned herein, are the apricots 'Patterson' (U.S. Plant Pat. No. 2,877), 'Modesto' (U.S. Plant Pat. No. 2,543), 'Tracy' (U.S. Plant Pat. No. 3,062), 'Autumn Glory' (non-patented), 'Red Beaut' Plum (U.S. Plant Pat. No. 2,539) and the proprietary plumcot 4G436.

ORIGIN OF THE VARIETY

The new variety of interspecific tree, a combination of crosses between (*Prunus armeniaca* and *Prunus salicina*), was originated by us in our experimental orchard located near Modesto, Calif. from an open pollinated proprietary interspecific seedling selection with the identification number '192LD63'. The maternal parent (192LD63) originated from crosses of the following apricot parents 'Patterson' (U.S. Plant Pat. No. 2,877), 'Modesto' (U.S. Plant Pat. No. 2,543), 'Autumn Glory' (non-patented), 'Tracy' (U.S. Plant Pat. No. 3,062) and the proprietary plumcot '4G436'. The proprietary plumcot (4G436) originated from seed of an open pollinated 'Red Beaut' Plum (U.S. Plant Pat. No. 2,539). A large number of these open pollinated seedlings were budded on established trees of 'Nemaguard' Rootstock (non-patented) to enhance earlier fruit production and under close observation the present seedling exhibited desirable fruit and tree characteristics and was selected in 1996 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETIES

The present new variety of interspecific tree [(Apricot× Apricot)×Plumcot]×[unknown pollen] is of large size, vigorous, semi-spreading growth and a productive and regular bearer of large size, freestone fruit with very good flavor and eating quality. The fruit is further characterized by having an attractive yellow-orange color, holding firm on the tree 7 to 10 days after maturity (shipping ripe) and being relatively uniform in size and maturity throughout the tree, with the fruit maturing in the late maturity season. The fruit having good handling, storage and shipping quality, with an average Brix of 15.5°. In comparison to its interspecific maternal parent (192LD63), the fruit of the new variety is larger in size, is higher in Brix and is approximately 30 days later in maturity. In comparison to the commercial apricot parent 'Patterson' (U.S. Plant Pat. No. 2,877), the fruit of the new variety is larger in size and is approximately 40 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, usually pruned to 3 to 3.5 meters in height and width for economical harvesting of fruit.

*Vigor.*—Vigorous, growth of 1.5 to 2 meters in height the first growing season. Varies with type of soil, fertility, climatic conditions and cultural practices.

*Form.*—Semi-spreading, usually pruned to vase shape.

*Branching habit.*—Semi-spreading, crotch angle approximately 40°, increases with heavy crop load.

*Productivity.*—Productive, thinning and spacing of fruit necessary for desired marketable size. Fruit set varies with climatic conditions during blooming period.

*Bearer.*—Regular, adequate fruit set 4 consecutive years, no alternate bearing observed.

*Fertility.*—Self fertile, sets fruit under bags.

*Density.*—Medium dense, pruned to vase shape to allow sunlight to center of tree to enhance fruit color and health of fruit spurs.

*Hardiness.*—Tree grown in USDA Hardiness Zone 9. Hardy in all stone fruit growing areas of California. Winter chilling requirement approximately 850 hours at or below 45° F.

Trunk:

*Size.*—Large. Average circumference 67.3 cm at 27.9 cm above ground on a 6 year old tree.

*Stocky.*—Medium.

*Texture.*—Medium rough, becomes rougher with age.

*Color.*—Varies from 2.5Y 3/4 to 2.5Y 4/2.

Branches:

*Size.*—Medium. Average circumference 17.7 cm. at 0.7 meter above ground. Crotch angle approximately 40°, increases with heavy crop load.

*Surface texture.*—New growth smooth. Mature growth medium rough, becoming rougher with age.

*Lenticels.*—Average number 38 in a 25.8 sq cm area of branch. Average length 2.3 mm. Average width 1.5 mm. Color varies from 7.5YR 6/10 to 7.5 YR 6/8.

*Color.*—New growth varies from 2.5GY 5/6 to 10YR 5/6. Mature growth varies from 5YR 4/2 to 7.5 YR 4/2, varies with exposure to sun and age of growth.

Leaves:

*Size.*—Medium. Average length 74.4 mm. Average width 63.2 mm.

*Form.*—Ovate.

*Apex.*—Acuminate.

*Base.*—Cuneate.

*Margin.*—Doubly serrate.

*Thickness.*—Medium.

*Surface texture.*—Upper surface relatively smooth, slightly indented over midrib and leaf veins, glabrous. Lower surface relatively smooth, small ridges created by midrib and pinnate venation, glabrous.

*Petiole.*—Size — medium. Average length 20.4 mm. Average width 1.4 mm. Longitudinally grooved, very shallow. Surface — glabrous. Color varies from 5R 3/8 to 2.5GY 8/6, varies with amount of exposure to direct sunlight.

*Glands.*—Type — reniform. Size — medium. Average length 0.5 mm. Average diameter 0.4 mm. Average number 2, varies from 1 to 3. Located primarily the upper portion of the petiole and the base of leaf blade. Color varies from 2.5R 2/8 to 2.5YR 5/8.

*Color.*—Upper surface varies from 5GY 4/8 to 5GY 3/6. Lower surface varies from 5GY 5/6 to 5GY 4/4. Midvein color varies from 2.5GY 7/6 to 5GY 8/6.

Flower buds:

*Size.*—Medium to large. Average length 12.2 mm. Average diameter 8.3 mm.

*Hardiness.*—Hardy with respect to California winters.

*Form.*—Conical, becoming slightly elongated before opening.

*Pedicel.*—Average length 2.2 mm. Average width 2.0 mm. Color varies from 2.5GY 8/6 to 2.5GY 8/10.

*Color.*—Varies from 5RP 8/6 to 7.5RP 8/6.

*Number of buds per spur.*—Varies from 1 to 16, average number 6. Varies with age of spur.

Flowers:

*Size.*—Medium to large. Average height 16.4 mm. Average diameter 25.3 mm.

*Petals.*—Number 5, alternately arranged to sepals. Size — average length 12.5 mm. Average width 14.3 mm. Shape — orbicular. Margin — sinuate. Color varies from 5RP 8/6 to 7.5RP 9/2, fades with age. Both surfaces glabrous.

*Sepals.*—Number 5, alternately arranged to petals. Shape — triangular. Both upper and lower surfaces glabrous. Size — average length 5.3 mm. Average width 6.3 mm. Color — upper surface varies from 2.5R 6/6 to 2.5R 8/4. Lower surface varies from 2.5R 3/6 to 2.5R 3/8.

*Stamens.*—Average number per flower 32. Average filament length 9.7 mm. Filament color N 9.5/ (white). Anther color varies from 5Y 8.5/8 to 5Y 8.5/6.

*Pollen.*—Self fertile, sets fruit under bag. Color varies from 2.5Y 8/12 to 5Y 8.5/8.

*Pistil.*—Number — normally one. Surface — pubescent. Average length 15.8 mm. Position of stigma average of 0.8 mm above anthers. Color varies from 2.5GY 9/4 to 10Y 8/4.

*Fragrance.*—Very slight.

*Blooming period.*—Date of First bloom Feb. 25. 2005. Date of Petal Fall Mar. 7, 2005, varies slightly with climatic conditions.

*Color.*—Varies from 7.5RP 8/6 to 7.5RP 9/2, fades with age of flower.

*Number flowers per flower bud.*—Usually one.

*Pedicel.*—Average length 2.6 mm. Average width 2.4 mm. Color varies from 2.5GY 7/6 to 5GY 6/6.

Fruit:

*Maturity when described.*—Firm ripe.

*Date of fruit picking.*—Aug. 10, 2005.

*Date of last picking.*—Aug. 17, 2005, varies slightly with climatic conditions.

*Size.*—Large. Average diameter axially 67.0 mm. Average transversely in suture plane 78.2 mm. Average across suture plane 58.1 mm. Average weight 95.6 grams, varies slightly with fertility of the soil, amount of thinning and climatic conditions.

*Form.*—Slightly elongated, slightly flattened toward suture plane.

*Suture.*—Shallow, well sealed, extends from base to apex.

*Ventral surface.*—Distinct, lipped.

*Apex.*—Slightly retuse.

*Base.*—Varies from flat to slightly retuse.

*Cavity.*—Rounded to elongated in suture plane. Average depth 4.1 mm. Average diameter 7.7 mm.

Stem:

*Size.*—Small to medium. Average length 5.1 mm. Average diameter 2.7 mm.

*Color.*—Varies from 5GY 6/8 to 5GY 6/4.

Flesh:

*Ripens.*—Evenly.

*Texture.*—Flesh firmer near surface of skin, toward pit cavity smooth and juicy.

*Fibers.*—Few, small, tender.

*Firmness.*—Firm, comparable to the 'Patterson' Apricot (U.S. Plant Pat. No. 2,877).

*Aroma.*—Slight.

*Amydgalin.*—Undetected.

*Eating quality.*—Very good.

*Flavor.*—Very good, good balance between acid and sugar.

*Juice.*—Moderate amount, enhances flavor.

*Brix.*—Average Brix 15.5°, varies slightly with amount of fruit per tree and climatic conditions.

*Color.*—Varies from 10YR 7/10 to 10YR 7/12. Pit cavity varies from 5YR 7/8 to 7.5YR 6/10.

Skin:

*Thickness.*—Medium.

*Surface.*—Smooth.

*Down.*—Moderate pubescence, very short in length.

*Tendency to crack.*—None.

*Color.*—Varies from 7.5YR 7/10 to 7.5YR 6/14, skin slightly darker where exposed to direct sunlight.

*Tenacity.*—Tenacious to flesh.

*Astringency.*—Undetected.

Stone:

*Type.*—Freestone.

*Size.*—Medium to large. Average length 28.7 mm. Average width 21.8 mm. Average thickness 14.8 mm.

*Form.*—Obovoid.

*Base.*—Usually rounded, varies from rounded to straight.

*Apex.*—Usually rounded, varies from rounded to slight point. Average length 0.8 mm.

*Surface.*—Very slightly pitted throughout. A very shallow groove on each side of suture.

*Sides.*—Unequal, one side extending further from suture plane.

*Ridges.*—Very narrow, small ridge near groove on each side of suture.

*Tendency to split.*—None.

*Color.*—Varies from 7.5YR 3/2 to 7.5YR 3/4.

Kernal:

*Form.*—Ovoid.

*Taste.*—Bitter.

*Viability.*—Viable, embryo completely developed.

*Size.*—Medium. Average length 19.8 mm. Average width 13.4 mm. Average depth 7.4 mm.

*Skin.*—Color varies from 10YR 5/6 to 10YR 5/8.

Use: Dessert. Market, local and long distance.

Keeping quality: Relatively good, held firm in cold storage 14 days at 38° to 42° F. without shriveling, internal breakdown of flesh or appreciable loss of eating quality.

Shipping quality: Good, showed minimal flesh bruising or skin scarring during picking, packing and shipping trials.

Plant/fruit disease resistance susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct interspecific tree, substantially as illustrated and described, characterized by its large size, vigorous, semi-spreading growth and a productive and regular bearer of large fruit with very good flavor and eating quality; the fruit is further characterized by having firm flesh, good handling and shipping quality, holding firm on the tree 7 to 10 days after maturity (shipping ripe) and in comparison to its interspecific maternal parent (192LD63), the fruit is larger in size, higher in Brix and is approximately 30 days later in maturity.

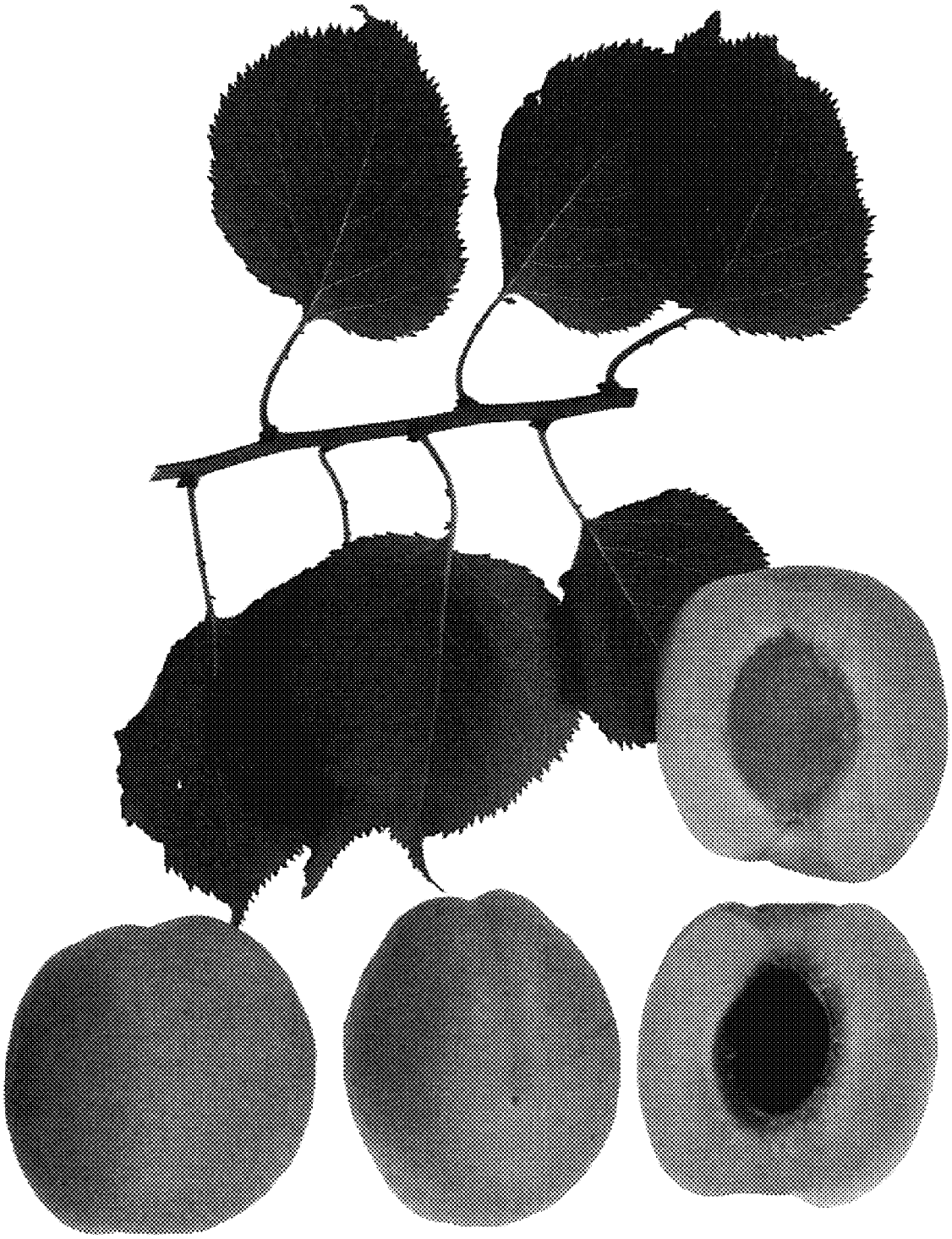

* * * * *